United States Patent [19]

Leiner et al.

[11] Patent Number: 5,080,865
[45] Date of Patent: Jan. 14, 1992

[54] ONE-WAY MEASURING ELEMENT

[75] Inventors: Marco J. Leiner; Karl Harnoncourt; Gerald Kirchmayer; Erich Kleinhappl; Helmut List, all of Graz; Hermann Marsoner, Steinberg; Otto S. Wolfbeis, Graz; Werner E. Ziegler, Graz, all of Austria

[73] Assignee: AVL AG, Schaffhausen, Switzerland

[21] Appl. No.: 390,754

[22] Filed: Aug. 8, 1989

[30] Foreign Application Priority Data

Aug. 9, 1988 [AT] Austria .................... A 2002/88

[51] Int. Cl.$^5$ ............... G01N 21/01; G01N 27/26; G01N 33/48; G01N 33/50
[52] U.S. Cl. ............................ 422/68.1; 422/82.02; 422/82.04; 422/83; 422/98; 436/68; 204/401; 204/409; 204/411
[58] Field of Search .......... 422/61, 68.1, 82.02, 422/82.04, 82.11, 82.12, 83, 98, 99, 100; 436/68; 204/401, 409, 411; 73/864.82, 864.86, 864.87, 1 R, 1 G

[56] References Cited

U.S. PATENT DOCUMENTS

| | | | |
|---|---|---|---|
| 3,638,109 | 1/1972 | Harnoncourt | 422/82.04 |
| 4,289,648 | 9/1981 | Hoskins et al. | 422/83 |
| 4,627,893 | 12/1986 | Cormier et al. | 204/401 |
| 4,654,127 | 3/1987 | Baker et al. | 422/82.02 |
| 4,786,394 | 11/1988 | Enzer et al. | 204/411 |
| 4,841,974 | 6/1989 | Gumbrecht et al. | 436/68 |
| 4,871,439 | 10/1989 | Enzer et al. | 204/411 |

FOREIGN PATENT DOCUMENTS 3004347  8/1980  Fed. Rep. of Germany ... 73/864.86

Primary Examiner—David L. Lacey
Assistant Examiner—Kimberly A. Trautman
Attorney, Agent, or Firm—Watson, Cole, Grindle & Watson

[57] ABSTRACT

In order to improve a one-way measuring element, which may be inserted into an analyzer for analyzing gaseous or liquid samples and which comprises a measuring channel with a measuring zone and one or more sensors located therein, the proposal is put forward that the one-way measuring element be provided with a sensor part whose measuring channel has seals on both ends, and with a sample-taking part, and that a coupling element be placed at the inlet end of the measuring channel for direct coupling of the sample-taking part containing the gaseous or liquid sample, and that the measuring channel be filled with a calibrating and storage medium prior to the measuring process, and that the calibrating and storage medium contained in the measuring channel be displaced by the sample flowing in after the sample-taking part has been coupled to the sensor part. The one-way measuring elements obtained in this way are characterized by great simplicity of design and ease of handling.

37 Claims, 3 Drawing Sheets

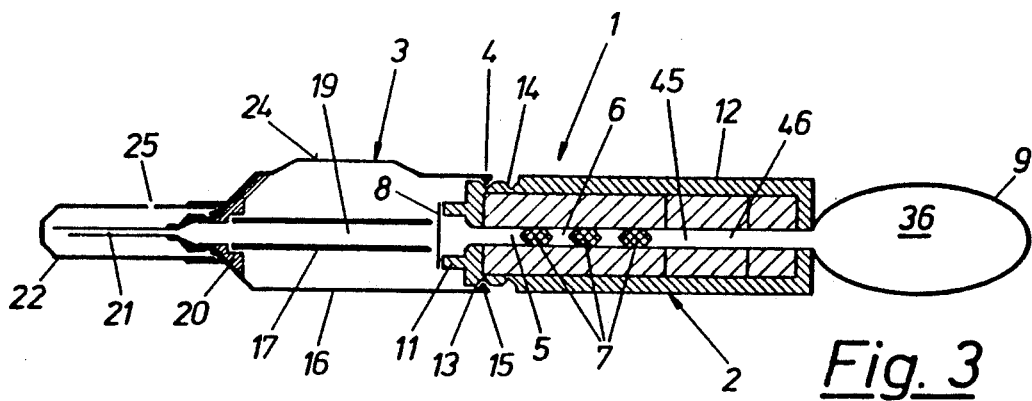
Fig. 3
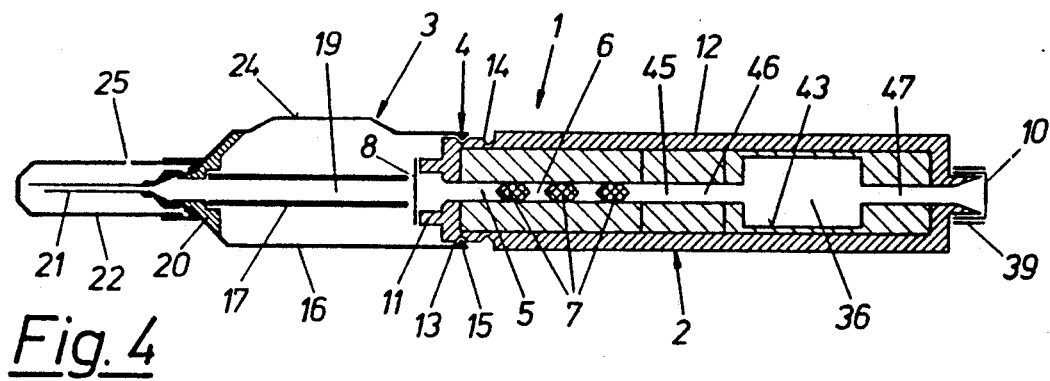
Fig. 4
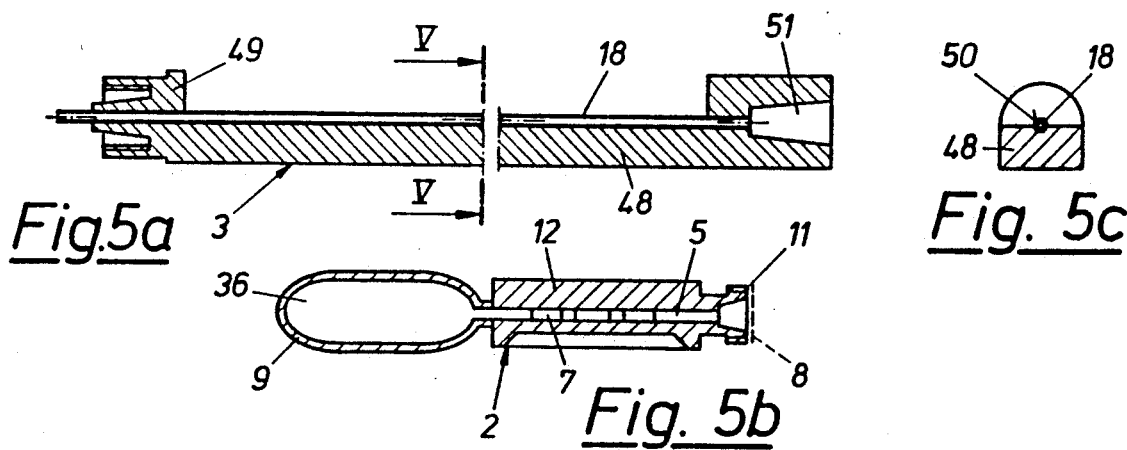
Fig. 5a
Fig. 5b
Fig. 5c
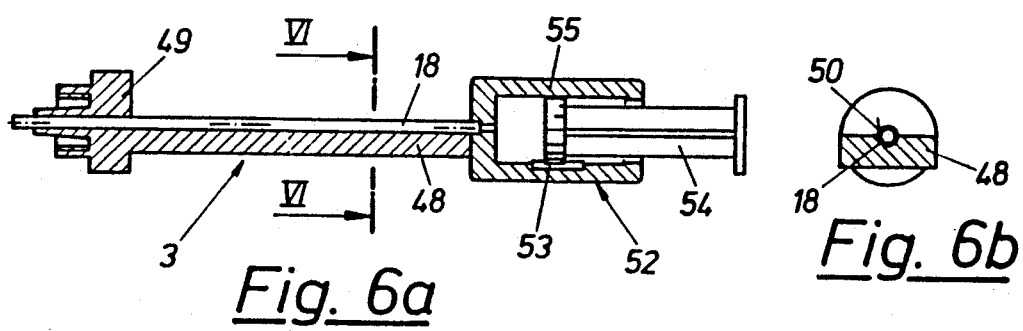
Fig. 6a
Fig. 6b

ONE-WAY MEASURING ELEMENT

BACKGROUND OF THE INVENTION

This invention relates to a one-way measuring element which may be inserted into an analyzer for analyzing gaseous or liquid samples and which comprises a measuring channel with a measuring zone and one or more sensors located therein.

DESCRIPTION OF THE PRIOR ART

A measuring element of the above type for clinical analyses is described in U.S. Pat. No. 4,654,127. On a base plate of the one-way measuring element inserted into an analyzing unit a measuring channel is placed which is configured as a capillary tube and is provided with several electrochemical sensors in a measuring area. The inlet of the measuring channel may be connected to a container subdivided into two chambers, one of them containing a calibrating solution and the other one the sample to be analyzed. Each chamber has an opening that is sealed by a pierceable diaphragm and may be put into contact with the inlet of the measuring channel.

After the sample has been introduced into the sample chamber the container is moved, for instance by rotation, from an initial position, in which none of the chambers communicates with the measuring channel, to a calibrating position, and the diaphragm sealing the calibrating container is pierced and the calibrating solution is drawn into the measuring area by means of the capillary forces acting in the measuring channel, and subsequently analyzed. By further rotation of the container the sample chamber is brought into contact with the inlet of the measuring channel and the sample is introduced into the measuring channel for analysis after the diaphragm has been pierced. The values obtained from the sample and calibrating liquids are used for determining the quantities to be measured in the sample.

The disadvantage of this known type of measuring element is its complicated design and the ensuing difficulties in handling it. Especially in blood gas analysis the complicated method of filling blood from a sample withdrawal element, for instance, a syringe or a capillary, into the sample chamber, from where it will enter the measuring channel only after further manipulation, is not to be recommended, since the blood gas values obtained may prove to be inaccurate because of the sample being exposed to ambient air, and reproducible results may be difficult to obtain. By effecting sample transport by means of capillary forces only, the calibrating solution cannot be reliably prevented from mixing with the sample, which may lead to measuring errors. In addition, infections of the operating personnel due to the handling of contaminated blood samples cannot be excluded, which must be considered a grave disadvantage in view of various blood-transmitted virus diseases.

SUMMARY OF THE INVENTION

It is an object of the invention to avoid such disadvantages and to propose a one-way measuring element of a simple design permitting mass production, which will enable manipulations during sample withdrawal and measurement to be kept at a minimum, in addition to offering a short and direct sample passage between the point of sample withdrawal and the measuring zone in the measuring channel.

In the invention this object is achieved by providing the one-way measuring element with a sensor part whose measuring channel has seals on both ends, and with a sample-taking part, and by placing a coupling element at the inlet end of the measuring channel for direct coupling of the sample-taking part containing the gaseous or liquid sample, and by filling the measuring channel with a calibrating and storage medium prior to the measuring process itself, and by providing that the calibrating and storage medium contained in the measuring channel be displaced by the sample flowing in after the sample-taking part has been coupled to the sensor part. Preferably, the measuring channel of the sensor part is already filled with the calibrating medium during storage, which will eliminate the need for any containers for calibrating media or the means for feeding such media into the measuring channel. Besides, the sensitive sensors are perfectly protected by the storage medium during stand-by or storage of the one-way or disposable measuring element. As the measuring channel is sealed on both ends a calibrating gas may be used instead of a calibrating liquid.

According to the inventin a steam-saturated gas-mixture at atmospheric pressure may be used as a calibrating and storage medium containing $O_2$ at 60-160 mm Hg, i.e., preferably at 90 mm Hg, and $CO_2$ at 20-60 mm Hg, i.e., preferably 35 mm Hg, as well as an inert gas, preferably nitrogen.

The advantages of this variant, especially when optical sensors are used for measuring the pH level, $CO_2$ content and $O_2$ content in blood, are that varying the overall pressure will yield two partial pressures each, thus permitting a two-point calibration, and that for a given composition values are used for calibration which closely approach the physiological standard values or expected values, thus permitting a most accurate analysis in this range, as well as that practically no mixing with blood will occur and that a gaseous calibrating medium is displaced most easily by the blood sample.

In applications justifying a greater calibrating effort water vapor-saturated air may be used as a calibrating and storage medium whose $O_2$ and $CO_2$ partial pressures are those prevailing at standard atmospheric conditions. In such instances the packaging of the one-way measuring element need not be gas-tight but only impermeable to steam.

Besides, the measuring element as described by the invention does not require a sample container as the sample will directly pass from a sample-taking part into the measuring channel of the sensor part, thereby preventing the sample parameters from being distorted by the exposure to ambient air and eliminating the danger of contamination of the operating personnel. The number of openings to be put into contact or couplings to be established for delivery of the calibrating and sample media is reduced to a minimum, leaving only the sample-taking part to be coupled to the sensor part.

A further development of the invention provides that the measuring channel of the sensor part be sealed in the area of the coupling by a first gas-tight diaphragm, which may be pierced by a sample channel holding the sample in the sample-taking part, and that the sensor part be provided with a reservoir containing the calibrating and storage medium, or rather, the sample, which reservoir should be connected to the outlet end of the measuring channel. Sealing in the coupling area may be achieved easily by means of a gas-tight diaphragm which is pierced when the sample-taking part is being connected. The sample quantity introduced into the measuring channel will displace the calibrating medium contained therein, which will be pushed into a reservoir on the outlet end of the sample channel together with any sample surplus.

In a further development of the invention the sensor part may be sealed at the outlet of the measuring channel by means of a second gas-tight, pierceable diaphragm, and a collecting chamber may be provided as a reservoir for the calibrating and storage medium, or rather, for the sample, between measuring channel and second diaphragm, and the sensor part may be made to connect to a suction device of the analyzer after the second diaphragm has been pierced. In this variant the sensor part includes a collecting chamber adjacent to the measuring channel. Via a channel leading away from the collecting chamber, which channel is initially sealed by a pierceable diaphragm, the sensor part is connected to the suction device of the analyzer. This channel leading away from the collecting chamber may be provided with an optical device measuring the filling level, which will prevent any calibrating or sample liquid from entering the analyzer.

According to a further variant of the invention a flexible diaphragm may be provided in the collecting chamber of the sensor part in order to prevent the calibrating and storage medium from leaving the measuring element. In this instance the second pierceable diaphragm and any filling level metering devices will not be needed. The calibrating and storage medium is kept in the measuring element by the pierceable diaphragm on the inlet end and by the flexible diaphragm in the collecting chamber on the outlet end.

Another version of the invention provides that the reservoir be configured as a balloon cooperating with a squeezing mechanism in the analyzer, a change in the shape of the balloon being accompanied by a volume enlargement of the reservoir. In a preferred form parts of the suction device and the reservoir for the calibrating medium are integrated in a single unit. The analyzer itself contains only a mechanism for enlarging the balloon, which is flat in its position of rest.

In a particularly favorable variant of the invention the sensor part and the sample-taking part are configured as an integral unit, the sample channel of the sample-taking part ending in front of the first pierceable diaphragm of the sensor part in a calibrating position, and connecting with the coupling element leading into the measuring channel in a measuring position, i.e., after the first diaphragm has been pierced. In this way the entire measuring element exposed to the sample forms a unit, thereby permitting integrated sample withdrawal and measuring. In the instance of such integrated sample withdrawal and measuring the sample-taking part is connected with the sensor part so as to be inseparable, but the two parts may still be shifted along or turned around the longitudinal axis. Coupling of the sample channel of the sample-taking part to the measuring channel of the sensor part may be effected in the analyzer itself, by pressing the two parts together by means of a mechanism in the analyzer.

The obvious advantages of this are: no manual coupling of sample-taking part and sensor part, therefore minimum handling, no leaking of the sample, above all, no contact with blood samples.

It may be proposed in a variant of the invention, for example, that the sample-taking part be provided with a hollow needle with a removable cap, which should be located on the same axis as the sample channel contained in a housing, and that a catch consisting of grooves and a projecting element be formed on the housing of the sensor part and on that of the sample-taking part, which will lock the sample-taking part in calibrating position, or rather, in measuring position after it has been shifted axially. In this instance the hollow needle is an integral component of the one-way measuring element and need not be disposed of separately after sample withdrawal and analysis. When the sample has been taken the protective cap is slipped back on the needle and the entire unit is inserted into the analyzer. Transfer of the sample into the sensor part takes place on the end of the sample-taking part opposite of the needle.

In an integrated sampling and measuring procedure with the suction device being located in the analyzer the steps to be followed are:

(1) Remove one-way measuring element with integrated sample-taking/sensor unit from its package;
(2) Remove cap from hollow needle;
(3) Take sample;
(4) Put back cap on hollow needle;
(5) Insert one-way measuring element into the analyzer;
(6) Analyzer will automatically couple sensor part to the suction device;
(7) Calibration of sensors;
(8) Analyzer will automatically couple the sample-taking part to the sensor part;
(9) Analyzer will suck the sample into the measuring channel of the sensor part;
(10) Measurement;
(11) Remove and discard one-way measuring element.

As regards calibration (cf. item 7), a multipoint calibration, preferably a two-point calibration, may be performed if a calibrating gas is used, provided that the suction system of the analyzer has a barometer fitting, and calibration is performed using differential pressure values.

In this context two particular variants are conceivable, i.e., variant (a), in which the sample channel is a capillary glass tube and the housing of the sample-taking part has a vent, and variant (b), in which the sample channel is a glass tube and the housing of the sample-taking part has a flexible zone which may be pressed in order to obtain the reduced pressure in the glass tube required for sample withdrawal. In variant (a) with the glass capillary as a sample channel, the sample is passed into the sample channel partly as a result of the prevailing capillary forces and partly as a result of the sample pressure (blood pressure). In variant (b) the flexible zone in the housing of the sample-taking part is slightly compressed, for instance with the thumb, and the reduced pressure developing after the slight pressure is released, is used for drawing in the sample.

In some applications it may be necessary to perform calibration before or during the sample-taking process. In order to gain time the measuring element could be calibrated before it is inserted into the analyzer. Since in the instance of optical sensors the measuring element should not be removed from the analyzer for sample-taking between the calibrating and the measuring process because of the danger of dust entering the coupling area of the optical waveguides, the proposal is put forward in a further variant of the invention that the separate sample-taking part configured as a puncturing kit be provided with a glass capillary and a connecting element for fitting a hollow needle, which connecting element should be able to be connected to the coupling element of the sensor part after the sample has been taken and the hollow needle has been removed. In the instance of non-integrated sample-taking and measuring the sensor part and the sample-taking part are separate units which are joined in the analyzer either by hand or automatically only after the sample has been taken. For this purpose the sensor part must first be placed in a special chamber in the analyzer and sealed by a cover. If the coupling is to be effected manually the coupling area of the sensor part must project from this chamber and the user must have access to it from outside. If the coupling is to be established by the analyzer itself, the sample-taking part is put into a second chamber preferably adjacent to the first one, and is then coupled by means of a mechanism in the analyzer. In this way calibration before, during or after sample withdrawal is guaranteed.

In a procedure with non-integrated sample-taking typical steps to be followed are:
(1) Remove sensor part from its package and insert it into the analyzer;
(2) Analyzer will automatically couple sensor part to the suction device;
(3) Calibration of sensors; meanwhile
(4) Remove sample-taking part from its package;
(5) Remove cap from hollow needle;
(6) Take sample, remove and discard needle;
(7) Insert sample-taking part into the analyzer;
(8) Analyzer will automatically couple the sample-taking part to the sensor part (via needle fitting);
(9) Analyzer will suck the sample into the measuring channel of the sensor part;
(10) Measurement;
(11) Remove and discard sensor part and sample-taking part.

Of course the two parts may also be coupled manually outside of the analyzer. In this case the user must puncture the diaphragm sealing the measuring channel. Then the parts which have been joined outside of the analyzer are inserted into the device. This procedure will not have the advantages of non-integrated sample withdrawal, however, i.e., independent sample-taking and calibration.

In a special variant of a non-integrated measuring and sample-taking unit according to the invention the end of the sample-taking part opposite of the connecting element is provided with a syringe connected to the glass capillary, which syringe will serve as a pressure device for introducing the sample into the measuring channel after the sample-taking part has been coupled to the sensor part. In this variant the analyzer need not be provided with a suction device. After the unit, i.e., the measuring element and the puncturing kit coupled thereto including the plunger-type syringe, has been inserted into the analyzer, the sample is automatically delivered from the sample-taking part to the measuring channel of the sensor part by a shifting of the plunger. It would also be possible to attach the sample-taking part after the sample has been taken and the needle has been removed, to a sensor part kept in permanent readiness in the analyzer, and to introduce the sample manually by pressing the plunger.

In order to obtain reproducible values from samples whose parameters to be measured have a marked temperature dependency, provisions are made that the capillary glass tube be embedded in a supporting element of the sample-taking part over most of its length but only with part of its circumference, and that the exposed part of the glass capillary be connected to a thermostat control in the analyzer.

In a further variant of the invention which is characterized by great simplicity of design, both inlet and outlet of the measuring channel are situated on the side of the sensor part facing the sample-taking part, and the outlet of the measuring channel is provided with a further coupling sealed by a gas-tight, pierceable diaphragm, and the measuring channel is filled with a liquid calibrating and storage medium, a glass capillary of the sample-taking part being insertable into one of the coupling openings, while a glass tube filled with an absorption medium may be introduced into the other coupling opening. For example, the measuring channel in the sensor unit may be U-shaped, the two coupling openings at the inlet and outlet of the measuring channel, which are located on the same outer surface of the sensor part, being sealed by a joint pierceable diaphragm. After calibration has been completed a sample-taking part is inserted into a coupling opening and a glass-tube filled with an absoprtion medium, such as filtering wool, is inserted into another coupling opening, both either manually or automatically, i.e., by the analyzer. Via the absorption effect of the filtering wool the sample is delivered to the sensors in the measuring zone of the measuring channel.

According to the invention the calibrating and storage medium may be an aqueous solution equilibrated with $O_2$ and $CO_2$.

For greater ease of handling the glass capillary of the sample-taking part and a glass capillary filled with filtering wool and serving as a suction device may be aligned parallel and held by a joint spacer and gripping piece.

As in former versions the sample-taking part and the sensor part could be integrated into one unit in this variant, if in further development the glass capillary of the sample-taking part and the glass capillary filled with filtering wool are located in one housing, and if the housing of the sensor part and that of the sample-taking part are provided with a catch consisting of grooves and a projecting element, which will arrest the two glass capillaries in calibrating position in front of the gas-tight diaphragm and in measuring position in the two coupling openings of the measuring channel.

In another variant of the invention the proposal is put forward that the inlet and outlet openings of the measuring channel be located on the side facing the sample-taking part, and that another coupling element be provided at the outlet end of the measuring channel, and that the coupling openings on the inlet and outlet ends be sealed by conical projections of the sample-taking part, and that the sample-taking part have a sample channel with a fitting for the hollow needle as well as a collecting chamber, and further that, after the sample-taking part has been de-coupled from the sensor part and rotated through 180 degrees and re-attached to the sensor part, connections for the collecting chamber and the sample channel should lock into the coupling openings of the sensor part. In this variant the sample-taking part may be coupled in two positions to the sensor part containing a U-shaped measuring channel. In a first position the inlet and outlet couplings of the sensor part are sealed by projections of the sample-taking part. In a second position, in which the sample-taking part is rotated through 180 degrees and put back in place again, the inlet of the measuring channel is coupled to the sample channel and the outlet of the measuring channel is coupled to a collecting chamber in the sample-taking part. The sample-taking part may have an integrated hollow needle, or it may be provided with a fitting for a needle to be inserted by the user.

Finally, it may be provided in all variants of the invention that the measuring channel of the sensor part have a zone for temperature and filling level measurement, which should be located behind the measuring zone in the direction of sample flow. Level measurement may be performed with the use of a photoelectric barrier, especially in non-transparent samples, such as blood. Even in optically transparent samples optical detectors may be employed, for instance, if differences in light refraction are utilized. For temperature measurement a temperature sensor of the analyzer is applied to a part of the surface of the sensor unit; from the readings of this temperature sensor the sample temperature may be deduced. In addition, materials of good thermal conductivity may be used in the temperature measuring zone of the measuring element.

Finally, an optical sensor could be used which would indicate the temperature via the change in fluorescence extinction time.

DESCRIPTION OF THE DRAWINGS

Following is a more detailed description of the invention as illustrated by the accompanying drawings, in which FIGS. 3, 4 are variants of the one-way measuring element in FIG. 1, FIGS. 5a, 5b show a one-way measuring element with separate sample-taking and sensor parts, FIG. 5c gives a section along V—V in FIG. 5a, FIG. 6a shows a variant according to FIG. 5a, FIG. 6b gives a section along line VI—VI in FIG. 6a, FIGS. 7a, 7b show a one-way measuring element with separate sample-taking and sensor parts.

DETAILED DESCRIPTION OF PREFERRED EMBODIMENTS

Figure 1:
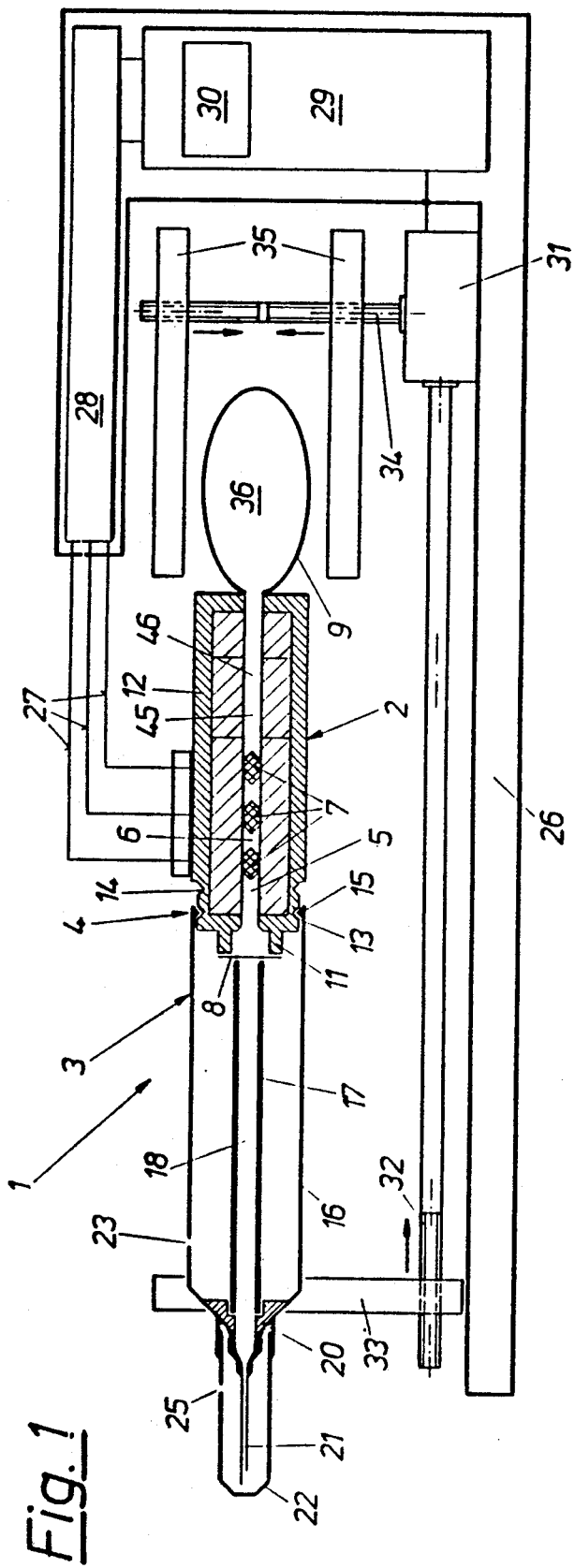
FIG. 1 is a schematic representation of a one-way measuring element as described by the invention, with an integrated sensor/sample-taking unit inserted in an analyzer.

The variants of the one-way measuring element 1 presented in FIGS. 1-4 each comprise a sensor part 2 combined with a sample-taking part 3 to form an integrated unit. Sensor part 2 and sample-taking part 3 are connected via a catch 4 which may lock in the calibrating position shown here and in a measuring position.

During storage of the individually packaged one-way measuring element the measuring channel 5 containing sensors 7 in the measuring zone 6 is filled with a calibrating and storage medium, which is prevented from leaving the sensor part by seals 8, 9, 10 at the inlet and outlet of the measuring channel 5. The inlet of the measuring channel 5, which is provided with a coupling element 11 for direct coupling of the sample-taking part 3, is sealed by a pierceable, gas-tight diaphragm 8, while the outlet of the measuring channel is sealed by a deformable, flexible balloon 9 in FIGS. 1 and 3, and another pierceable, gas-tight diaphragm 10 in FIGS. 2 and 4.

The housing 12 of the sensor part 2 is provided with grooves 13, 14 cooperating with a projecting element 15 on the housing 16 of the sample-taking part 3; in the calibrating position, which is also maintained during storage of the one-way measuring element, the projecting element 15 engages with groove 13 of the catch 4. In this position the sample channel 17 of the sample-taking part 3 will end immediately in front of the pierceable diaphragm 8, coaxial with the measuring channel 5 and the coupling element 11. The end of the sample channel 17 facing away from the diaphragm 8—which channel 17 may be constituted by a capillary glass tube 18 (FIGS. 1 and 2) or a glass tube 19 (FIGS. 3 and 4)—is held by the housing 16 of the sample-taking part 3, a fitting 20 for a hollow needle 21 being provided in this area. The hollow needle 21 is protected by a removable cap 22.

After the one-way measuring element 1 has been taken out of its package the cap 22 of the hollow needle 21 is removed and a sample is withdrawn. The sample is sucked in either by the capillary forces of the capillary glass tube 18 according to FIGS. 1 or 2—the housing 16 having a vent 23 for pressure compensation in this instance—or it is actively delivered into the glass tube 19 by the user pressing a flexible zone of the housing 16.

After the sample has been taken the cap 22, which also has a vent 25, is put back on the needle, and the measuring element is inserted into an analyzer 26 represented schematically in FIG. 1, where the optical sensors 7 used in this variant are brought into contact with optical waveguides 27.

The values obtained from an excitation and measuring device 28 (not shown here in detail) of the analyzer 26 are processed in a control and evaluation unit 29 and are displayed via a display or printing unit 30.

The invention would also permit the use of electrochemical sensors in the measuring zone 6 of the measuring channel 5. In this instance suitable electrical contacts would have to be provided instead of optical pick-ups when the measuring element 1 is plugged into the analyzer.

In the variant shown in FIG. 1 the individual sensors are calibrated with the use of the calibrating medium contained in the measuring channel.

After calibration the sample-taking part 3 is automatically coupled to the sensor part 2 by means of the analyzer 26. For this purpose a grip 33 is moved by means of a spindle 32 turned by a motor 31, thereby shifting the sample-taking part 3 axially into measuring position, in which the projecting element 15 of the housing 16 engages in the groove 14 of the sensor part 2. As a consequence of the axial shift the capillary glass tube 18 holding the sample in the sample-taking part 3 will pierce the diaphragm 8 of the sensor part 2 and will thus be connected to the coupling element 11 of the sensor part 2.

By means of another spindle 34 driven by the same motor 31 a squeezing mechanism 35 is actuated which will effect a change in the shape of the flexible balloon 9, such that the volume of the reservoir 36 formed by the balloon 9 is enlarged and the sample is sucked from the sample channel 17 into the measuring zone 6 of the measuring channel 5. The reservoir 36 is simultaneously used for receiving the calibrating medium and any sample surplus. An advantage of this variant is that no calibrating or sample media will enter the analyzer.

At the end of the measuring process the one-way measuring element is removed from the analyzer 26 and disposed of.

Figure 2B:
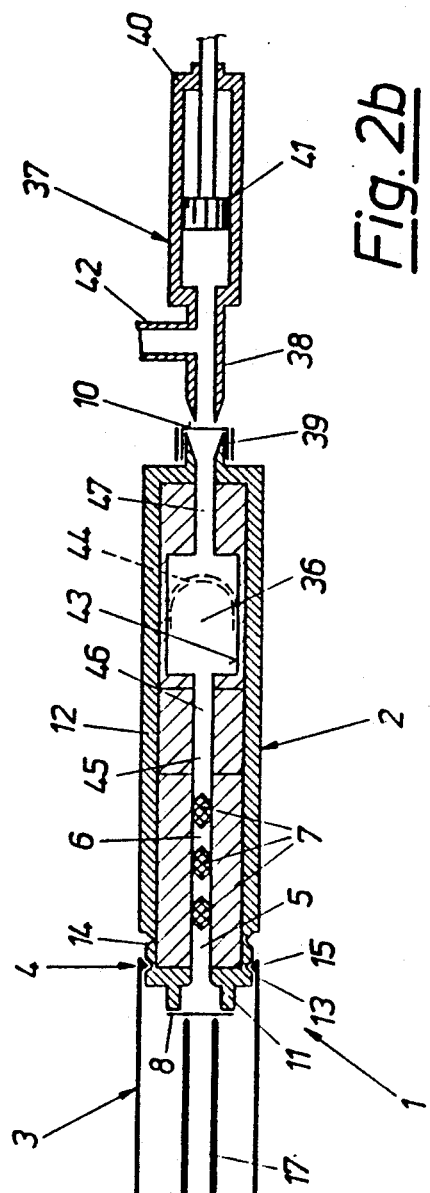
FIG. 2b shows a suction device of the analyzer.
Figure 2A:
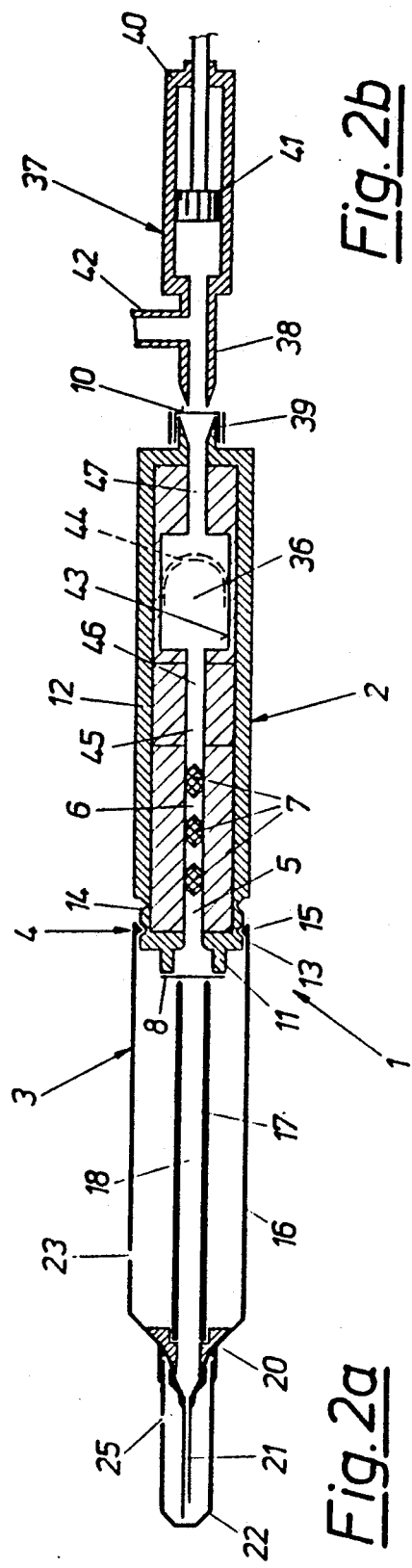
FIG. 2a shows a variant of the measuring element in FIG. 1.

The variant presented in FIGS. 2a, b differs from that in FIG. 1 by providing a further gas-tight, pierceable diaphragm 10 at the outlet of the measuring channel 5. After the measuring element has been placed in the analyzer a suction device 37 (cf. FIG. 2b) with a suction tube 38 is connected to a coupling element 39 of the sensor part 2. The suction device 37 has a plunger 41 guided in a cylinder 40, whose drive is not shown in this drawing. Via a barometer fitting 42 of the suction tube 38 it will be possible to perform a two-point calibration, since two different pressure levels may be employed for calibration if a calibrating gas is used.

In order to avoid contamination of the analyzer the reservoir 36 is designed for use as a collecting chamber 43 between the measuring channel 5 and the diaphragm 10.

It will also be possible to provide a flexible diaphragm 44 in the collecting chamber, which will prevent any leakage of the calibrating and storage media, and will thus render unnecessary the pierceable diaphragm 10.

Next to the measuring zone 6 of the measuring channel 5 areas 45, 46 are provided for measuring temperature and filling level. In variants according to FIG. 2a, which do not have a flexible diaphragm 44 in the collecting chamber 43, a further area 47 may be provided for overflow control. Suitable means for checking filling levels and overflow would be photoelectric barriers, for example; the simplest way of measuring temperature is on the outside of the housing 12 of the sensor part 2.

In all subsequent variants identical parts have identical reference numbers. In the variants shown in FIGS. 5a–5c, and 6a, 6b the sample-taking part 3 configured as a puncturing kit and the sensor part 2 are delivered in separate packages and are coupled only after sample withdrawal.

The sample-taking part 3 is provided with a capillary glass tube 18 that is embedded in a supporting element 48 and serves as a sample channel, to which is attached a connecting element 49 onto which a hollow needle (not shown here) may be fitted. After the sample has been taken and the hollow needle has been removed the sample-taking part 3 is connected via the connecting element 49 to the coupling element 11 of the sensor part 2 and the diaphragm 8 is pierced. The capillary glass tube is only half embedded in the supporting element 48 over most of its length, and the exposed part 50 of the capillary shown mainly in FIGS. 5c and 6b is brought into contact with a thermostat control (not shown here) after the measuring element has been inserted into the analyzer. On the end opposite of the connecting element 49 the sample-taking part 3 has a safety volume 51 which will receive any sample surplus collecting upon puncturing. The individual coupling and connecting elements 8, 49 may be configured as Luer seals.

On the end opposite of the connecting element 49 the sample-taking part 3 presented in FIGS. 6a and 6b has a syringe 52 which is connected to the capillary glass tube 18. While the sample is drawn through the capillary the pressure compensation necessary for this operation is effected via a groove 53 between the plunger 54 and the cylinder 55 of the syringe 52. After the sample-taking part 3 has been coupled to the sensor part 2 the syringe is used as a pressure device for feeding the sample into the measuring channel of the sensor part either automatically or manually.

Figure 7A:
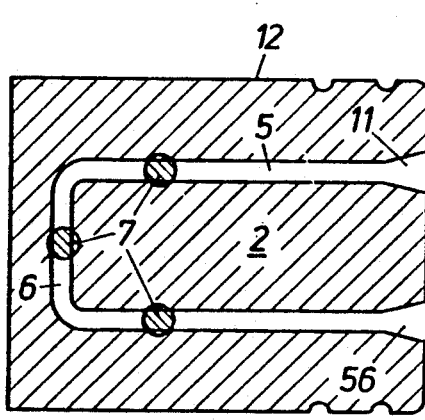
Figure 7B:
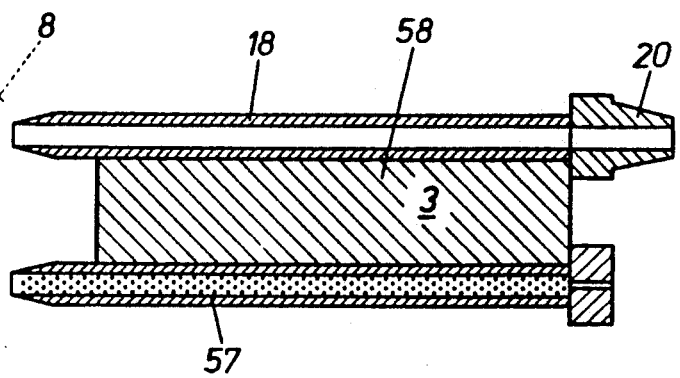
Figure 8:
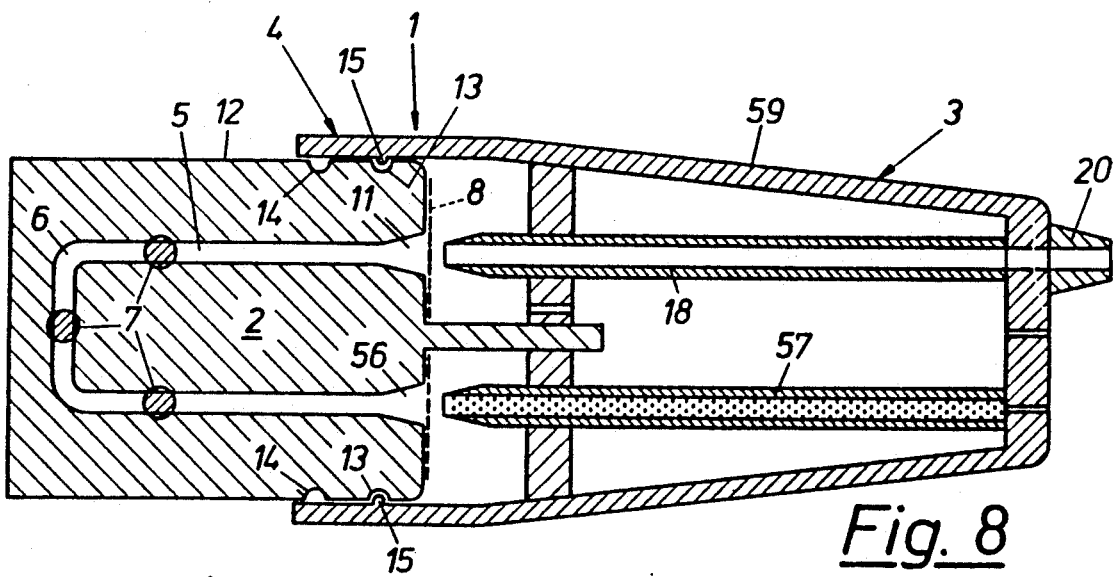
FIG. 8 presents a one-way measuring element with integrated sensor/sample-taking unit.
Figure 9:
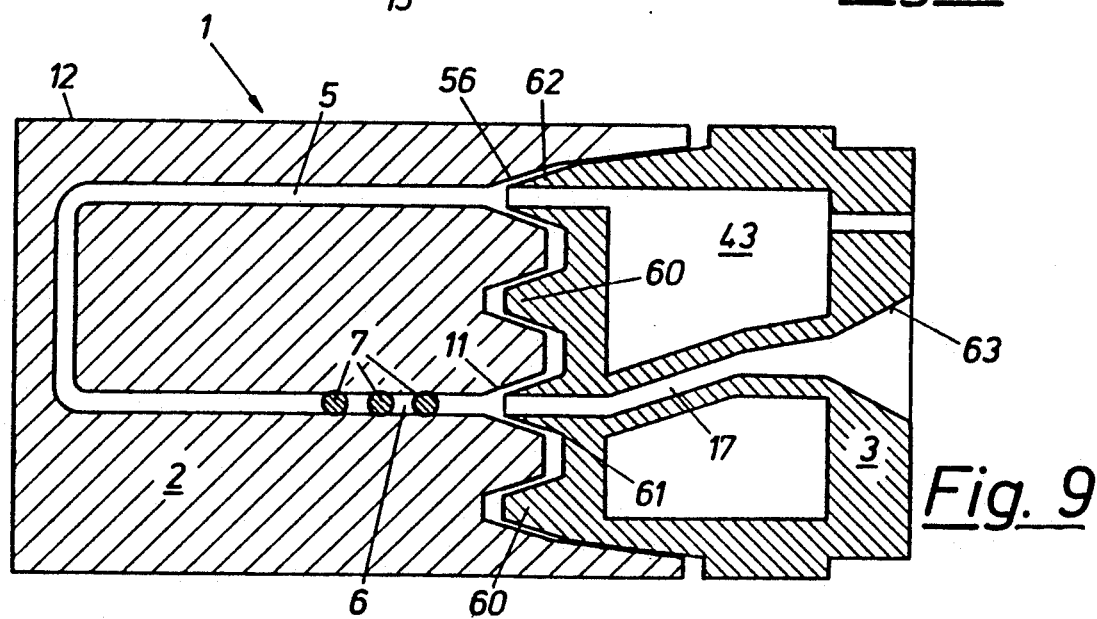
FIG. 9 presents a further one-way measuring element.

In FIGS. 7–9 the sensor part 2 has a U-shaped masuring channel 5. Both inlet and outlet of the measuring channel 5 are on the end of the sensor part 2 facing the sample-taking part 3.

In the variants according to FIGS. 7 and 8 a further coupling element 56 for receiving a capillary glass tube 57 that is filled with filtering wool and serves as a suction device for sample transport, is situated next to the coupling element 11 for connecting the capillary glass tube 18 of the sample-taking part 3. Initially both coupling elements 11, 56 are sealed by a joint pierceable diaphragm 8. Only after insertion of the capillary glass tubes 18 and 57, which are jointly held in a spacer piece 58 (cf. FIG. 7b), the sample will enter the measuring zone 6 of the measuring channel 5 and thus reach the sensors 7 located in this zone. On the end facing away from the sensor part 2 the sample-taking part 3 is provided with a fitting 20 for a hollow needle.

As is seen in FIG. 8 the above variant again permits an integrated measuring/sample-taking unit. In this instance the capillary glass tube 18 and the capilalry glass tube 57 filled with filtering wool are located in a housing 59 which may be fixed in two positions on the housing 12 of the sensor part 2 by means of a catch 4 in the same way as is shown in FIGS. 1–4. In the calibrating position, when the projecting element 15 is enganged in the groove 13, the two capillary glass tubes 18 and 57 are held in front of the gas-tight diaphragm 8, whereas in the measuring position, when the capillaries 18 and 57 connect to the coupling elements 11 and 56, having pierced the diaphragm 8, the projecting element 15 engages the groove 14. Since in this case sample transport is due to the absorption effect of the filtering wool, liquid calibrating and storage media must be used.

In the measuring element 1 presented in FIG. 9 the coupling elements 11, 56 on the inlet and outlet end of the measuring channel 5 are sealed in calibrating position by conical projections 60 of the sample-taking part 3. After the sample-taking part 3 has been de-coupled from the sensor part 2 and rotated by 180°, the two parts may be re-connected, upon which—in measuring position—connections 61 and 62 provided for the measuring channel 17 and a collecting chamber 43 will lock with the coupling elements 11 and 56 of the sensor part 2. Sample transport is then effected via suction and pumping devices that have been described above but are not shown here. The conical connecting element for a sample withdrawal needle has the reference number 63.

We claim:

1. A one-way measuring element which is insertable into an analyzer for analyzing gaseous or liquid samples, wherein said one-way measuring element comprises a sensor part and a sample-taking part, said sensor part comprising a measuring channel with an inlet end, an outlet end and a measuring zone with at least one sensor located in said zone, said measuring channel being provided with seals on both of said ends and containing a calibrating and storage medium prior to measurement, and wherein a coupling element is placed at said inlet end of said measuring channel for direct coupling of said sample-taking part containing said gaseous or liquid sample, said measuring channel of said sensor part being sealed in the area of said coupling element by a first gas-tight diaphragm which is pierced by a sample channel of said sample-taking part, said sensor part further being sealed at said outlet end of said measuring channel by means of a second gas-tight, pierceable diaphragm wherein a collecting chamber is positioned between said measuring channel and said second gas-tight diaphragm, said collecting chamber comprises a reservoir for said calibrating and storage medium, and wherein said sensor part is connectable to a suction device of the analyzer after said second gas-tight diaphragm has been pierced, and wherein said outlet end of said measuring channel of said sensor part is provided with the reservoir receiving said calibrating and storage medium and wherein said calibrating and storage medium contained in said measuring channel is displaced by said sample flowing in after said sample-taking part is coupled to said sensor part.

2. A one-way measuring element according to claim 1, wherein said sensor part and said sample-taking part are configured as a connectable unit, said sample-taking part including a sample channel ending in front of said first gas-tight diaphragm of said sensor part when in a calibrating position, and said sample channel, after piercing said first gas-tight diaphragm, connecting with said coupling element which leads into said measuring channel of said sensor part when in a measuring position.

3. A one-way measuring element according to claim 2, wherein said sample-taking part comprising said sample channel is contained in a housing and is provided with a hollow needle with a removable cap and said sensor part is contained in a housing, and wherein a catch consisting of grooves and a projecting element is formed on said housing of said sensor part and on said housing of said sample-taking part; so that said catch arrests said sample-taking part in said calibrating position and in said measuring position after said sample-taking part has been shifted axially toward said sensor part.

4. A one-way measuring element according to claim 3, wherein said sample channel is a capillary glass tube and said housing of said sample-taking part has a vent.

5. A one-way measuring element according to claim 3, wherein said sample channel is a glass tube and said housing of said sample-taking part has a flexible zone positioned and arranged so that when it is pressed a reduced pressure will exist in said glass tube for sample withdrawal.

6. A one-way measuring element according to claim 1, wherein a flexible diaphragm is provided in said collecting chamber of said sensor part, to prevent said calibrating and storage medium and said sample from leaving said one-way measuring element.

7. A one-way measuring element according to claim 1, wherein said sample-taking part and said sensor part are separable, said sample-taking part being configured as a puncturing kit, which is provided with a capillary glass tube and a connecting element for fitting a hollow needle, said connecting element being constructed so as to be connected to said coupling element of said sensor part after said hollow needle is removed.

8. A one-way measuring element according to claim 7, wherein said sample-taking part includes syringe means connected to said glass capillary on the end opposite of said connecting element, said syringe means defining a pressure device for introducing said sample into said measuring channel after said sample-taking part has been coupled to said sensor part.

9. A one-way measuring element according to claim 7, wherein said capillary glass tube is partly embedded in a supporting element of said sample-taking part, such that an embedded and an exposed part are provided, and wherein said exposed part of said capillary glass tube is connectable to a thermostat control means in the analyzer.

10. A one-way measuring element according to claim 1, wherein said calibrating and storage medium comprises a water-vapor-saturated gas mixture at atmospheric pressure containing $O_2$ at 60–160 mm Hg, $CO_2$ at 20–60 mm Hg, and an inert gas.

11. A one-way measuring element according to claim 10, wherein said calibrating and storage medium consists of 90 mm Hg $O_2$, 35 mm Hg $CO_2$ and nitrogen.

12. A one-way measuring element according to claim 1, wherein said calibrating and storage medium comprises water-vapor-saturated air whose $O_2$ and $CO_2$ partial pressures are those prevailing at standard atmospheric conditions.

13. A one-way measuring element according to claim 1, wherein said inlet end and said outlet end of said measuring channel are situated on one side of said sensor part facing said sample-taking part, said measuring channel being filled with said liquid calibrating and storage medium, and said outlet end of said measuring channel includes a further coupling element sealed by said second gas-tight, pierceable diaphragm, wherein a glass capillary tube is contained in said sample-taking part and is insertable into one of said coupling elements, and further including an additional glass tube filled with an absorption medium positioned and arranged so as to be insertable into said further coupling element.

14. A one-way measuring element according to claim 13, wherein said liquid calibrating and storage medium comprises an aqueous solution equilibrated with $O_2$ and $CO_2$.

15. A one-way measuring element according to claim 13, wherein the additional capillary glass tube is filled with filtering wool and said capillary glass tube of said sample-taking part and said additional capillary glass tube filled with filtering wool are aligned parallel and held by a joint spacer and gripping piece.

16. A one-way measuring element according to claim 15, wherein said sensor part and said sample-taking part are configured as a connectable unit, said capillary glass tube of said sample-taking part and the additional capillary glass tube filled with filtering wool being located in one housing, and said sensor part located in an additional housing, a catch means comprising grooves and a projecting element being formed on the additional housing of the sensor part and on the housing of said sample-taking part, said catch arresting the capillary glass tube of said sample-taking part and the additional capillary glass tube filled with filtering wool in a calibrating position in front of said first and second gas-tight diaphragms and in a measuring position when the capillary glass tube of said sample-taking part and the additional capillary glass tube filled with filtering wool are coupled with the measuring channel.

17. A one-way measuring element according to claim 1, wherein said measuring channel of said sensor part has a zone for temperature and filling level measurement means, which is located downstream from said measuring zone.

18. A one-way measuring element according to claim 1, wherein at least one optical sensor is provided in said measuring zone of said measuring channel.

19. A one-way measuring element according to claim 18, wherein said at least one optical sensor is a plurality of optical sensors are provided in said measuring channel of said sensor part, which are used for measuring the pH level, $CO_2$ content and $O_2$ content of a blood sample.

20. A one-way measuring element which is insertable into an analyzer for analyzing gaseous or liquid samples, wherein said one-way measuring element comprises a sensor part and a sample-taking part, said sensor part comprising a measuring channel with an inlet end, an outlet end and a measuring zone with at least one sensor located in said zone, said measuring channel being provided with seals on both of said ends and containing a calibrating and storage medium prior to measurement, and wherein a coupling element is placed at said inlet end of said measuring channel for direct coupling of said sample-taking part containing said gaseous or liquid sample, said measuring channel of said sensor part being sealed in the area of said coupling element by a first gas-tight diaphragm which is pierced by a sample channel of said sample-taking part, and wherein said outlet end of said measuring channel of said sensor part is provided with a reservoir receiving said calibrating and storage medium, said reservoir configured as a balloon for cooperating with a squeezing mechanism in said analyzer, wherein a change in the shape of said balloon is accompanied by a volume enlargement of said reservoir.

21. A one-way measuring element according to claim 20, wherein said sensor part and said sample-taking part are configured as a connectable unit, said sample-taking part including a sample channel ending in front of said first gas-tight diaphragm of said sensor part when in a calibrating position, and said sample channel, after piercing said first gas-tight diaphragm, connecting with said coupling element which leads into said measuring channel of said sensor part when in a measuring position.

22. A one-way measuring element according to claim 21, wherein said sample-taking part comprising said sample channel is contained in a housing and is provided with a hollow needle with a removable cap and said sensor part is contained in a housing, and wherein a catch consisting of grooves and at projecting element is formed on said housing of said sensor part and on said housing of said sample-taking part; so that said catch arrests said sample-taking part in said calibrating position and in said measuring position after said sample-taking part has been shifted axially toward said sensor part.

23. A one-way measuring element according to claim 22, wherein said sample channel is a capillary glass tube and said housing of said sample-taking part has a vent.

24. A one-way measuring element according to claim 22, wherein said sample channel is a glass tube and said housing of said sample-taking part has a flexible zone positioned and arranged so that when it is pressed a reduced pressure will exist in said glass tube for sample withdrawal.

25. A one-way measuring element according to claim 20, wherein said sample-taking part and said sensor part are separable, said sample-taking part being configured as a puncturing kit, which is provided with a capillary glass tube and a connecting element for fitting a hollow needle, said connecting element being constructed so as to be connected to said coupling element of said sensor part after the hollow needle is removed.

26. A one-way measuring element according to claim 25, wherein said sample-taking part includes syringe means connected to said glass capillary on the end opposite of said connecting element, said syringe means defining a pressure device for introducing said sample into said measuring channel after said sample-taking part has been coupled to said sensor part.

27. A one-way measuring element according to claim 25, wherein said capillary glass tube is partly embedded in a supporting element of said sample-taking part, such that an embedded and an exposed part are provided, and wherein said exposed part of said capillary glass tube is connectable to a thermostat control means in the analyzer.

28. A one-way measuring element according to claim 20, wherein said calibrating and storage medium comprises a water-vapor-saturated gas mixture at atmospheric pressure containing $O_2$ at 60-160 mm Hg, $CO_2$ at 20-60 mm Hg, and an inert gas.

29. A one-way measuring element according to claim 28, wherein said calibrating and storage medium consists of 90 mm Hg $O_2$, 35 mm Hg $CO_2$ and nitrogen.

30. A one-way measuring element according to claim 20, wherein said calibrating and storage medium comprises water-vapor-saturated air whose $O_2$ and $CO_2$ partial pressures are those prevailing at standard atmospheric conditions.

31. A one-way measuring element according to claim 20, wherein said measuring channel of said sensor part has a zone for temperature and filling level measurement means, which is located downstream from said measuring zone.

32. A one-way measuring element according to claim 20, wherein at least one optical sensor is provided in said measuring zone of said measuring channel.

33. A one-way measuring element according to claim 32, wherein said at least one optical sensor is a plurality of optical sensors are provided in said measuring channel of said sensor part, which are used for measuring the pH level, $CO_2$ content and $O_2$ content of a blood sample.

34. A one-way measuring element which is insertable into an analyzer for analyzing gaseous or liquid samples, wherein said one-way measuring element comprises a sensor part and a sample-taking part, said sensor part comprising a measuring channel with an inlet end, an outlet end and a measuring zone with at least one sensor located in said zone, said measuring channel being provided with seals on both of said ends and containing a calibrating and storage medium prior to measurement, and wherein a coupling element is placed at said inlet end of said measuring channel for direct coupling of said sample-taking part containing said gaseous or liquid sample, and wherein said calibrating and storage medium contained in said measuring channel is displaced by said sample flowing in after said sample-taking part is coupled to said sensor part, said inlet end and said outlet end of said measuring channel being situated on one side of said sensor part facing said sample-taking part, and wherein a further coupling element is provided at said outlet end of said measuring channel, and wherein the two coupling elements on said inlet and said outlet ends are sealed by conical projections of said sample-taking part, and wherein said sample-taking part comprises a sample channel with a fitting for a hollow needle and further comprising a flow connector element, and said sample-taking part further comprising a collecting chamber having a flow connector element, said sample channel and said collecting chamber being constructed and arranged such that when said sample-taking part has been de-coupled from said sensor part and rotated through 180 degrees and re-attached to said sensor part, said connector elements will lock with said coupling elements of said sensor part.

35. A one-way measuring element according to claim 34, wherein said measuring channel of said sensor part has a zone for temperature and filling level measurement means, which is located downstream from said measuring zone.

36. A one-way measuring element according to claim 34, wherein at least one optical sensor is provided in said measuring zone of said measuring channel.

37. A one-way measuring element according to claim 36, wherein said at least one optical sensor is a plurality of optical sensors are provided in said measuring channel of said sensor part, which are used for measuring the pH level, $CO_2$ content and $O_2$ content of a blood sample.

* * * * *